(12) United States Patent
Itoh et al.

(10) Patent No.: US 7,092,091 B2
(45) Date of Patent: Aug. 15, 2006

(54) METHOD OF EVALUATING OPTICAL INFORMATION MEDIUM

(75) Inventors: Hidetake Itoh, Tokyo (JP); Kazushi Tanaka, Tokyo (JP)

(73) Assignee: TDK Corporation, Tokyo (JP)

( * ) Notice: Subject to any disclaimer, the term of this patent is extended or adjusted under 35 U.S.C. 154(b) by 0 days.

(21) Appl. No.: 11/074,762

(22) Filed: Mar. 9, 2005

(65) Prior Publication Data

US 2005/0180281 A1 Aug. 18, 2005

Related U.S. Application Data

(63) Continuation of application No. PCT/JP04/03221, filed on Mar. 11, 2004.

(30) Foreign Application Priority Data

Mar. 18, 2003 (JP) .............................. 2003-074553

(51) Int. Cl.
*G01N 21/00* (2006.01)

(52) U.S. Cl. ..................................................... 356/338

(58) Field of Classification Search .................... None
See application file for complete search history.

(56) References Cited

U.S. PATENT DOCUMENTS

| | | | | |
|---|---|---|---|---|
| 5,589,858 A | * | 12/1996 | Kadowaki et al. | ............ 347/14 |
| 5,807,944 A | * | 9/1998 | Hirt et al. | .................... 526/279 |
| 2001/0041242 A1 | | 11/2001 | Hayashida et al. | |
| 2004/0234720 A1 | | 11/2004 | Hayashida et al. | |
| 2005/0013965 A1 | | 1/2005 | Itoh et al. | |

FOREIGN PATENT DOCUMENTS

| | | |
|---|---|---|
| EP | 0 552 636 A1 | 7/1993 |
| EP | 1146510 A1 | 10/2001 |
| JP | 4-339333 | 11/1992 |
| JP | 6-44617 | 2/1994 |
| JP | 6-349119 | 12/1994 |
| JP | 8-248024 | 9/1996 |
| JP | 9-100111 | 4/1997 |
| JP | 9-212913 | 8/1997 |
| JP | 10-110118 A | 4/1998 |
| JP | 10-302311 | 11/1998 |
| JP | 11-185313 | 7/1999 |
| JP | 11-293159 A | 10/1999 |
| JP | 2000-17572 A | 1/2000 |
| JP | 2000-82236 | 3/2000 |
| JP | 2001-228302 A | 8/2001 |
| JP | 2002-157784 | 5/2002 |
| JP | 2002-230837 | 6/2002 |

(Continued)

OTHER PUBLICATIONS

TDK Homepage, http://www.tdk.co.jp/, Oct. 28, 2002.

(Continued)

*Primary Examiner*—Tu T. Nguyen
(74) *Attorney, Agent, or Firm*—Oblon, Spivak, McClelland, Maier & Neustadt, P.C.

(57) ABSTRACT

A method for evaluating an optical information medium by judging quantitatively and reproducibly the surface quality of the optical information medium by the use of a novel artificial fingerprint liquid as an evaluation dispersion liquid including: adhering, under predetermined conditions, the evaluation dispersion liquid; measuring a recording/reproducing characteristic (e.g. error rate) of the medium with the evaluation dispersion liquid droplets adhered to the medium surface; and judging the optical information medium as an acceptable medium when the measured recording and/or reproducing characteristic is equal to, or better than, a predetermined value.

2 Claims, 2 Drawing Sheets

FOREIGN PATENT DOCUMENTS

| | | |
|---|---|---|
| JP | 2002-190136 A | 7/2002 |
| JP | 2003-22571 | 1/2003 |
| JP | 2003-168248 | 6/2003 |
| JP | 2004-35824 | 2/2004 |
| JP | 2004-152418 | 5/2004 |
| JP | 2004-171711 | 6/2004 |
| JP | 2004-171741 | 6/2004 |
| JP | 2004-185772 | 7/2004 |
| WO | WO 03/029382 A1 | 4/2003 |
| WO | WO 2004/040564 A1 | 5/2004 |

OTHER PUBLICATIONS

Naoki Hayashida, et al. "Functional Hard-Coat for Cartridge-Free DVR Blue", Joint International Symposium on Optical Memory and Optical Data Storage Technical Digest IEEE Catalog 02EX552 ISBN #0-7803-7379-0, Jul. 2002, pp. 12-14.

Naoki Hayashida, et al. "High-Performance Hard Coat for Cartridge-Free Blu-Ray Disc" Japanese Journal of Applied Physics vol. 42, Feb. 2003, pp. 750-753.

Naoki Hayashida, et al. "Anti-Fingerprint Property of the Hard-Coat for Cartridge-Free Blu-Ray Disc" Optical Data Storage, May 2003, pp. 18-20.

Naoki Hayashida, et al. "Anti-Fingerpring Property of the Hard-Coat for Cartridge-Free Blu-Ray Disc" Optical Data Storage, vol. 5069, SPIE 0277-786X/03, May 2003, pp. 361-368.

The Association of Powder Process Industry and Engineering, Japan, "Appie Jis Test Powders", Sep. 30, 2003 w/English transistion.

* cited by examiner

METHOD OF EVALUATING OPTICAL INFORMATION MEDIUM

CROSS-REFERENCE TO RELATED APPLICATIONS

This is a continuation application of PCT/JP2004/003221, filed Mar. 11, 2004, which was published under PCT Article 21(2) in Japanese, the entire content of which is hereby incorporated by reference.

TECHNICAL FIELD

The present invention relates to a method for evaluating an optical information medium, and more specifically, to a simple method for evaluating an optical information medium by judging the surface quality of the medium by the use of a novel artificial fingerprint liquid as an evaluation dispersion liquid.

BACKGROUND ART

When an optical disk such as a reproduction-only optical disk, optical recording disk, magneto-optical recording disk, and the like, is used, the adhesion of stains or fingerprints to the surface thereof is caused on the basis of various stain materials. The adhesion of these stains or fingerprints is unpreferable, and in some cases, the surface of the optical disk is subjected to an appropriate surface treatment in order to improve an anti-staining property thereof, decrease a fingerprint adhering property or improve a fingerprint removing property.

For example, investigations are being made on various water repellent or oil repellent treatments to the surface of the optical disk. In order to check the effect of improving the anti-staining property by the surface treatments, in many cases, there is used a manner of adhering a fingerprint actually onto the optical disk surface and, then, evaluating the wiping-off property thereof with the naked eye. However, such an evaluating manner is poor in quantitativeness and reproducibility.

On the assumption that if the water repellency or the oil repellency of the optical disk surface is high, stain materials are easily removed, the following is frequently performed: measurement of the contact angles of various liquids, such as water and aliphatic hydrocarbons, to the above treated-surface. However, the evaluation based on the contact angle or surface free energy is, in a sense, an indirect evaluating manner. Accordingly, it can be properly used as a manner for evaluating the anti-staining property in only a highly restricted case where the above-mentioned assumption that if the water repellency or the oil repellency is high, excellent anti-staining property is exhibited comes into effect. This evaluating manner gives only a relative evaluation result at best. In other words, when this evaluating manner is applied to an optical disk surface, it is substantially impossible that a threshold value which represents whether or not the disk can be used without causing any practical problem is determined for the contact angle or surface free energy.

In recent years, it has been desired that about optical information media the recording density thereof is made higher in order to store a mass of data such as moving image data. Thus, researches and developments are being actively made for making the density of recording capacity higher. As one of them, the following suggestion is made: as seen in, for example, a DVD, the recording/reproducing wavelength thereof is made short and the numerical aperture (NA) of the objective lens is made large, thereby making the condensed spot diameter of the reproducing/reproducing beam small. As compared with a CD, a recording capacity (4.7 GB/surface) 6 to 8 times that of the CD is actually attained by changing the recording/reproducing wavelength from 780 nm to 650 nm and changing the numerical aperture (NA) from 0.45 to 0.60. Recently, as a method for recording high-quality moving images for a long time, an attempt has been made to make the recording/reproducing wavelength short up to about 400 nm and making the numerical aperture high up to 0.85, so as to attain a recording capacity 4 times or more that of DVD.

However, when the recording density is made high in this way, the condensed spot diameter of the recording/reproducing beam becomes small. Consequently, the recording medium becomes more sensitive to dust, dirt, fingerprints or the like adhering to the laser beam incident side surface of the medium than the conventional art. In particular, about stains containing an organic material, such as fingerprints, a large effect is produced when the stains adhere to the laser beam incident side surface. Since the stains are not easily removed, many countermeasures have been considered so far.

For example, Japanese Laid-open Patent Publication Nos. 10-110118 (1998) and 11-293159 (1999) suggest that when a hard coat agent coated film is formed on a surface of an optical disk substrate made of polycarbonate or the like, a non-crosslinking type fluorine type surfactant is incorporated into the hard coat agent. In order to evaluate the anti-staining property of the hard coat surface of the optical disk, there is performed an operation of adhering an artificial fingerprint liquid wherein a small amount of sodium chloride, urea and lactic acid is dissolved in a mixture solution of water and ethanol onto the surface of the hard coat under pressure, using a pseudo fingerprint, and then determining the wiping-off property thereof with the naked eye. This artificial fingerprint liquid is a liquid described in JIS K2246: 1994 "Rust Preventing Oil". The JIS standard prescribes a performance-testing method for rust preventing oils used for temporary rust-prevention of metal materials such as steel. Accordingly, the artificial fingerprint liquid is prepared to determine the corrosiveness of metal materials. For this reason, the liquid is not useful at all for purposes other than this. Even if the artificial fingerprint liquid made mainly of water and ethanol is adhered onto a surface of an optical disk substrate made of resin such as polycarbonate, in reality the artificial fingerprint liquid is repelled and is not fixed on the substrate surface in almost all cases. It can be considered from this fact that the resin substrate surface exhibits the same wiping-off property against. the artificial fingerprint liquid whether the surface is not subjected to any surface treatment or is subjected to surface treatment. That is, it is hardly significant to use the artificial fingerprint liquid prescribed in JIS K2246: 1994 for evaluation of the anti-staining property or the fingerprint removing property of an optical disk surface.

From such an actual situation, it is desired to develop an artificial fingerprint liquid for quantitatively and with a good reproducibility evaluating the surface quality of an optical disk. It is also desired to develop a simple evaluating method for quantitatively and reproducibly judging the surface quality of an optical disk by the use of the artificial fingerprint liquid.

DISCLOSURE OF THE INVENTION

OBJECTS OF THE INVENTION

Thus, an object of the present invention is to solve the above-mentioned problems of the conventional art and provide a simple method for evaluating an optical information medium by judging quantitatively and reproducibly the surface quality of the optical information medium by the use of a novel artificial fingerprint liquid as an evaluation dispersion liquid.

SUMMARY OF THE INVENTION

The present invention comprises the following inventions.

(1) A method for evaluating an optical information medium, comprising the steps of:

adhering, under predetermined conditions, an evaluation dispersion liquid containing a fine-particle-form substance and a dispersion medium capable of dispersing the fine-particle-form substance onto the surface of the optical information medium which is on the incident side of a recording and/or reproducing beam;

measuring an area ratio of the medium surface occupied with the evaluation dispersion liquid droplets adhered per unit area of the medium surface; and judging the optical information medium as an acceptable medium when the measured area ratio is 6% or less.

(2) A method for evaluating an optical information medium, comprising the steps of:

adhering, under predetermined conditions, an evaluation dispersion liquid containing a fine-particle-form substance and a dispersion medium capable of dispersing the fine-particle-form substance onto the surface of the optical information medium which is on the incident side of a recording and/or reproducing beam;

measuring a recording and/or reproducing characteristic of the medium with the evaluation dispersion liquid droplets adhered to the medium surface; and judging the optical information medium as an acceptable medium when the measured recording and/or reproducing characteristic is equal to, or better than, a predetermined value.

(3) A method for evaluating an optical information medium, comprising the steps of:

adhering, under predetermined conditions, an evaluation dispersion liquid containing a fine-particle-form substance and a dispersion medium capable of dispersing the fine-particle-form substance onto the surface of the optical information medium which is on the incident side of a recording and/or reproducing beam;

measuring the error rate as a recording and/or reproducing characteristic of the medium, with the evaluation dispersion liquid droplets adhered to the medium surface; and judging the optical information medium as an acceptable medium when the measured error rate is equal to, or smaller than, a predetermined value.

(4) The method for evaluating an optical information medium according to any one of the above (1) to (3), wherein the fine-particle-form substance contained in the evaluation dispersion liquid has an average particle size of 0.05 µm or more and 30 µm or less.

(5) The method for evaluating an optical information medium according to any one of the above (1) to (4), which is applied to the optical information medium intended for use in a system wherein the smallest diameter of the recording and/or reproducing beam on the surface which is on the incident side of the recording and/or reproducing beam is 500 µm or less.

(6) The method for evaluating an optical information medium according to any one of the above (1) to (4), which is applied to the optical information medium intended for use in a system wherein the smallest diameter of the recording and/or reproducing beam on the surface which is on the incident side of the recording and/or reproducing beam is greater than 500 µm.

The present invention provides a simple method for evaluating an optical information medium such as a reproduction-only optical disk, optical recording disk, magneto-optical recording disk, and the like, by judging quantitatively and reproducibly the quality of the recording/reproducing beam incident side surface of the optical information medium by the use of a novel artificial fingerprint liquid as an evaluation dispersion liquid.

MODES FOR CARRYING OUT THE INVENTION

Figure 1:
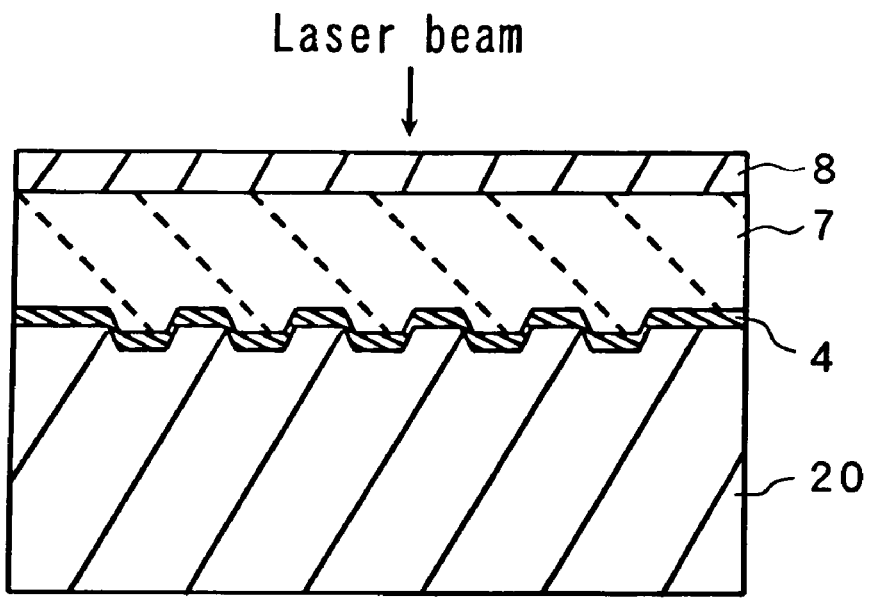
FIG. 1 is a schematic cross-sectional view illustrating a structural example of an optical information medium.

First, a novel artificial fingerprint liquid used as an evaluation dispersion liquid in the present invention is described.

The artificial fingerprint liquid used in the present invention comprises a fine-particle-form substance and a dispersion medium capable of dispersing the fine-particle-form substance. In the present description, the term "dispersion medium" refers only to a liquid component that remains as a pseudo-fingerprint component after the artificial fingerprint liquid has been transferred to the surface of an optical information medium to be evaluated, but not to a diluent that is optionally used when using the artificial fingerprint liquid, and is mostly or completely evaporated finally after the transfer of the artificial fingerprint liquid.

The dispersion medium preferably has a surface tension ranging from 20 to 50 mNm$^{-1}$ at 25° C. By such a constituent, the artificial fingerprint liquid is made up to an artificial fingerprint liquid having a character as close as possible to an actual fingerprint. Thus, the artificial fingerprint liquid can be suitably used for evaluating an anti-staining property, a fingerprint adhering property, or a fingerprint removing property on the surface of an optical disk to be evaluated.

In the case that an artificial fingerprint liquid of a homogeneous component system made only of a liquid is used at this time, the liquid does not approximate to the removing property of any actual fingerprint. For example, in the case that triolein, which is one of sebum-constituting components, is used as the homogeneous system, the surface tension of triolein is 34 mNm$^{-1}$ at 25° C. Therefore, the surface of polytetrafluoroethylene (PTFE), which has a critical surface tension of about 18 mNm$^{-1}$, repels triolein completely without getting wet. However, actual fingerprints never fail to be fixed even on the PTFE surface. This is mainly because any fingerprint is not made only of a liquid substance but is made of a heterogeneous system containing an insoluble material and a viscous material. Accordingly, by making a heterogeneous system wherein an appropriate insoluble component is added to a dispersion medium made of a liquid component contained in an actual fingerprint and/or a liquid similar thereto, the artificial fingerprint liquid having a character as close as possible to an actual fingerprint can be obtained.

Herein, critical surface tension will be described. The water repellency and the oil repellency of a material can be represented into one way by critical surface tension ($\gamma_c$/mNm$^{-1}$), which is a criterion of the surface free energy of the material. The critical surface tension can be obtained from an actually-measured value of the contact angle thereof. Specifically, the contact angle ($\theta$/rad) to a smooth surface made of a specified material is measured about several saturated hydrocarbon liquids each having a known surface tension (surface tension: $\gamma_1$/mNm$^{-1}$). A value extrapolated to cos $\theta$=1 in plots of cos $\theta$ and $\gamma_1$ is the critical surface tension $\gamma_c$ of the specified material. In order that some material can repel a liquid, it is necessary that the critical surface tension $\gamma_c$ of the material is less than the surface tension $\gamma_1$ of the liquid. For example, $\gamma_c$ of a material having a surface composition of a methylene chain (—$CH_2$—)n is 31 mNm$^{-1}$. Accordingly, the material repels water, which has a surface tension $\gamma_1$ of 73 mNm$^{-1}$ at a temperature of 20° C., but completely gets wet to n-hexadecane, which has a surface tension $\gamma_1$ of 28 mNm$^{-1}$ The contact angle thereof turns to 0 degree.

The artificial fingerprint liquid used in the present invention comprises a fine-particle-form substance in the dispersion medium. The majority of solid components contained in any actual fingerprint is a protein called keratin. In the simplest way, therefore, fine powders of keratin are added to and mixed with the dispersion medium having the above physical property values, so that the above-mentioned artificial fingerprint liquid can be prepared. Indeed, a mixture wherein keratin fine powders are mixed with a dispersion medium, such as water, oleic acid, squalane or triolein, at an appropriate ratio can be effectively used as the artificial fingerprint liquid of the present invention. However, generally available keratin is remarkably expensive. Thus, a large amount thereof cannot be easily obtained. Furthermore, commercially available keratin has a different particle size distribution from that of keratin contained in actual fingerprints. It is therefore necessary to adjust the particle size distribution thereof in advance if necessary. Accordingly, it cannot be necessarily said that the method of using commercially available keratin is a preferable method from the viewpoint of simplicity, measurement precision and its reproducibility.

In order to solve the problems of keratin, the present inventors researched a fine-particle-form substance which can be used instead of keratin. As a result, it has been found that fine particles having a good wettability to the dispersion medium having the above physical property values and having particle sizes close to that of keratin contained in actual fingerprint components are preferable as the fine-particle-form substance.

The artificial fingerprint liquid used in the present invention includes at least one selected from inorganic fine particles and organic fine particles as the fine-particle-form substance. The inorganic fine particles, which are not particularly limited, maybe, for example, silica fine particles, alumina fine particles, iron oxide fine particles, and mixtures of any two or more selected from the fine particles. The organic fine particles, which are not particularly limited, may be, for example, chitin fine particles, chitosan fine particles, acrylic type fine particles, styrene type fine particles, divinylbenzene type fine particles, polyamide type fine particles, polyimide type fine particles, polyurethane type fine particles, melamine type fine particles, and mixtures of any two or more selected from the fine particles.

All of the inorganic fine particles exhibit, as the constituting component of the artificial fingerprint liquid, the same effect as keratin fine particles, and are further more inexpensive than the keratin fine particles. Therefore, in order to decrease costs and make the performance stable, the content of the inorganic fine particles is preferably 50% by weight or more, more preferably 80% by weight or more, and considerably preferably 100% by weight of the whole of the fine-particle-form substance. It is advisable that organic fine particles may be used together if necessary. Among the organic fine particles, acrylic type fine particles, styrene type fine particles, divinylbenzene type fine particles, polyamide type fine particles, polyimide type fine particles, polyurethane type fine particles, melamine type fine particles and the like are preferable since they are relatively inexpensive. Further, keratin fine particles may be used together.

The fine-particle-form substance preferably has an average particle size (that is, median diameter) of 100 μm or less, and more preferably has an average particle size of 50 μm or less. Examples of the fine-particle-form substance which includes an inorganic component and has an average particle size of 100 μm or less include JIS Z8901 testing powders 1 and 2, ISO testing powder 12103-1, and the Association of Powder Process Industry and Engineering Japan (APPIE) standard powder. All the testing powders are preferable since they have uniform particle sizes and are available at a relatively low cost. Among examples of the JIS Z8901 testing powder 1, Kanto loam is preferable. It is allowable to use, besides the respective testing powders per se, at least one of inorganic fine particles contained in the respective testing powders, for example, at least one selected from various oxide fine particles such as $SiO_2$, $Fe_2O_3$ and $Al_2O_3$. The average particle size of the fine-particle-form substance is preferably 0.05 μm or more, more preferably 0.5 μm or more. Accordingly, the average particle size of the fine-particle-form substance is preferably 0.05 μm or more and 30 μm or less, more preferably 0.5 μm or more and 10 μm or less. If the fine-particle-form substance is too large or too small, the substrate cannot exhibit easily a sufficient function as an alternate material of keratin contained in actual fingerprints.

The fine-particle-form substance preferably has a critical surface tension at 25° C. larger than that of the used dispersion medium at 25° C., and the critical surface tension is preferably 40 mNm$^{-1}$ or more, more preferably 50 mNm$^{-1}$ or more. All of the above particles exemplified as the inorganic fine particles have such a desired nature about the critical surface tension.

In the present invention, as the dispersion medium, there is preferably used a liquid having a surface tension ranging from 20 to 50 mNm$^{-1}$ at 25° C. and a saturated vapor pressure of 760 mmHg (101325 Pa) or less at 200° C. The liquid which constitutes sweat or sebum of human beings or a liquid having a character close to it usually has such physical property values. Accordingly, it is advisable to use a liquid having the physical property values as the dispersion medium of the artificial fingerprint liquid in the present invention. If the surface tension is less than 20 mNm$^{-1}$ at 25° C., the wettability to the surface of an optical disk to be evaluated becomes too high, so that the artificial fingerprint liquid adheres far more easily onto the optical disk surface and is more difficultly removed than actual fingerprints. On the other hand, if the surface tension exceeds 50 mNm$^{-1}$ at 25° C., the wettability to the optical disk surface to be evaluated lowers, so that the artificial fingerprint liquid adheres far more difficultly onto the optical disk surface and is more easily removed than actual fingerprints.

If the saturated vapor pressure exceeds 760 mmHg (101325 Pa) at 200° C., the dispersion medium volatilizes gradually after the adhesion of the fingerprint onto the optical disk surface to be evaluated, so that the state of the adhering artificial fingerprint may change in a short time. What degree of easiness of the volatilization of the dispersion medium is after the adhesion of the fingerprint onto the optical disk surface to be evaluated is also affected by the temperature of the optical disk surface to be evaluated, the temperature of the use environment of the artificial fingerprint liquid, or the like.

In the present invention, it is desirable that the viscosity of the liquid used as the dispersion medium is preferably 500 cP or less, more preferably from 0.5 to 300 cP, and still preferably from 5 to 250 cP at 25° C. By having such a viscosity, the dispersion medium causes the fine-particle-form substance to be satisfactorily dispersed and be easily fixed to the optical disk surface even after the adhesion of the fingerprint onto the optical disk surface to be evaluated.

The dispersion medium is not particularly limited, and examples thereof include higher fatty acid, derivatives of higher fatty acid, terpenes, and derivatives of terpenes. Examples of the higher fatty acid include various acids such as oleic acid, linoleic acid, linolenic acid. The derivatives of higher fatty acid may be ester derivatives, and examples thereof include diglyceride derivatives and triglyceride derivatives (for example, triolein). The terpenes may be various terpenes, and examples thereof include squalane, limonene, α-pinene, β-pinene, camphene, linalool, terpineol, and cadinene. It is advisable to select at least one from these and use the selected one alone or the selected two or more in a mixture form. It is also preferable to mix one or more thereof with water and use the mixture.

In the present invention, an appropriate mixing ratio between the fine-particle-form substance and the dispersion medium depends on the method of adhering the artificial fingerprint liquid onto the optical disk surface to evaluated, which method will be described later, and others. Therefore, the mixing ratio cannot be specified without reservation. In general, however, 0.1 to 5.0 weights of the fine-particle-form substance are preferably added per weight of the dispersion medium, and 0.1 to 3.0 weights of the fine-particle-form substance are more preferably added, and 0.2 to 1.0 weights of the fine-particle-form substance are most preferably added. If the mixing ratio of the fine-particle-form substance to the dispersion medium is too low or too high, it becomes difficult that the resultant functions effectively as an artificial fingerprint liquid. If the fine-particle-form substance is at a ratio less than 0.1, the effect of the addition of the fine-particle-form substance is not obtained, so that the artificial fingerprint liquid is not easily fixed on the optical disk surface to be evaluated or the liquid tends to be easily removed even if the liquid is fixed. On the other hand, if the fine-particle-form substance is added at a ratio over 5.0, liquid crosslinking effect, based on the dispersion medium, on the optical disk surface to evaluated deteriorates, so that the artificial fingerprint liquid tends not to be easily fixed.

As mentioned above, the dispersion medium refers only to a liquid component that remains as a pseudo-fingerprint component after the artificial fingerprint liquid has been transferred to the optical disk surface to be evaluated, but not to a diluent which is described later.

In the present invention, it is also preferable to add a wax, that is, an ester of higher fatty acid and monovalent alcohol to these dispersion medium components, which are liquid at ambient temperature, so as to make the viscosity of the dispersion medium components high. As the wax, for example, the following may be used: a natural wax such as candelilla wax, carnauba wax, urucury wax, rice wax, sugar wax, wood wax, beeswax, spermaceti, Chinese insect wax, shellac wax, or montan wax; or a synthetic wax such as cholesteryl stearate, myristyl myristate, or cetyl palmitate. The addition percentage of each of the waxes may be appropriately determined in accordance with the property of the optical disk to be evaluated, for example, the property of the recording/reproducing optical system of the optical disk, the purpose of the evaluation, and others.

A general thickener may be added to the artificial fingerprint liquid, examples thereof including carrageenan, gum arabic, xanthan gum, galactomannan, and pectin. Furthermore, in order to improve the dispersibility of the fine-particle-form substance, various surfactants maybe added, examples thereof including quaternary ammonium salts, alkylbenzenesulfonates, and polyoxyethylene polyoxypropylene glycol.

In the present invention, the artificial fingerprint liquid may be diluted with a diluent such as isopropyl alcohol, methyl ethyl ketone or methoxypropanol if necessary in order to improve the transferring property of the artificial fingerprint. These diluents are mostly or completely evaporated finally after the transfer of the artificial fingerprint liquid to the optical disk surface to be evaluated. The diluent usually has a saturated vapor pressure exceeding 760 mmHg (101325 Pa) at 200° C. It is allowable to add ethanol, liquid paraffin or the like appropriately to the artificial fingerprint liquid.

In a way as described above, the artificial fingerprint liquid used in the present invention is composed.

A method is next described for transferring the artificial fingerprint liquid as the evaluation dispersion liquid onto the recording/reproducing beam incident side surface of the optical disk to be evaluated, under predetermined conditions, to form a pseudo-fingerprint.

In the present invention, when the artificial fingerprint liquid is adhered to the surface of the optical information medium to be evaluated, under predetermined conditions, it is preferable to use a pseudo-fingerprint transferring stamp made of elastomer. Specifically, it is preferable to produce a pseudo-fingerprint transferring stamp made of silicone rubber, butadiene rubber, urethane rubber or the like and use this. The pseudo-fingerprint transferring stamp may be made into such a shape that a fingerprint pattern is precisely copied from a mold which is actually obtained from man's fingers. In a simpler way, it is preferable to use a rubber plug for printing an artificial fingerprint liquid prescribed in JIS K2246-1994. That is, it is possible to use, as the pseudo-fingerprint transferring stamp, a material the surface of which is roughened by polishing a small circular surface (diameter: about 26 mm) of a No. 10 rubber plug with an AA240 abrasive material prescribed in JIS R6251 or JIS R6252 or a abrasive material having performance similar thereto. However, without limitation to the above-mentioned material, a material capable of giving substantially the same pseudo-fingerprint transferring property as described above can be preferably used. In order to obtain a size close to that of an actual fingerprint, an object having a smaller diameter than the above-mentioned rubber plug is preferably used.

Specifically, a rubber plug having a diameter of 8 to 25 mm is preferably used, and a rubber plug having a diameter of 8 to 20 mm is more preferably used.

The method of using such a pseudo-fingerprint transferring stamp to transfer the artificial fingerprint liquid, as a pseudo fingerprint, onto an optical disk surface under predetermined conditions, can be appropriately determined in accordance with the purpose of the evaluation. For example, a master plate for pseudo-fingerprint pattern transfer is previously produced, and the rubber plug is used to transfer a pseudo-fingerprint from this master plate onto the optical disk surface to be evaluated. Specifically, the artificial fingerprint liquid is uniformly applied onto a rigid substrate made of glass or resin. As the coating method at this time, an appropriate method may be used from various coating methods such as spin coating and dip coating methods. When the artificial fingerprint liquid is applied onto the substrate, the liquid may be diluted with an appropriate organic solvent such as isopropyl alcohol or methyl ethyl ketone in order to obtain a good application property. It is advisable to evaporate these diluents by air drying or heat drying after the application. In this way, the substrate onto which the artificial fingerprint liquid is uniformly applied is produced and this is used as a master plate for pseudo-fingerprint pattern transfer.

Under predetermined conditions, the artificial fingerprint liquid is transferred as a pseudo-fingerprint from the master plate for pseudo-fingerprint pattern transfer onto the surface of an optical disk to be evaluated by means of the pseudo-fingerprint transferring stamp. Procedures to carry out the transfer process are properly determined depending on the level of the surface characteristics required of the optical disk to be evaluated (i.e., anti-staining property, fingerprint adhering property, or fingerprint removing property), and/or the components and compositions of the artificial fingerprint liquid used. While such transfer procedures are not limited to particular procedures, independent procedures as described in the following Levels 1 through 4 may be used:

Level 1:

1. Transfer the artificial fingerprint liquid material applied to the surface of the master plate onto the pseudo-fingerprint transferring stamp by pressing the transferring stamp against the surface of the master plate on which the artificial fingerprint liquid is applied, under a predetermined load of 1 N to 35 N for a predetermined period of time. The load and the time over which the load is applied are properly determined.

2. Subsequently, transfer the pseudo-fingerprint pattern onto the surface of the optical disk to be evaluated by pressing the transferring stamp with the artificial fingerprint liquid material transferred on it against the surface of the optical disk, under a predetermined load of 1 N to 35 N for a predetermined period of time. The load and the time over which the load is applied are also properly determined.

Level 2:

1. Transfer the artificial fingerprint liquid material applied to the surface of the master plate onto the pseudo-fingerprint transferring stamp by pressing the transferring stamp against the surface of the master plate on which the artificial fingerprint liquid is applied, under a predetermined load of 1 N to 35 N for a predetermined period of time. The load and the time over which the load is applied are properly determined.

2. Subsequently, transfer a portion of the transferred artificial fingerprint liquid material onto the transferring stamp, onto the surface of a polycarbonate substrate (e.g., polcarbonate substrate that has an identical shape to the optical disk to be evaluated) by pressing the transferring stamp with the transferred artificial fingerprint liquid material against the surface of the polcarbonate substrate, under a predetermined load of 1 N to 35 N for a predetermined period of time. The load and the time over which the load is applied are also properly determined.

3. Subsequently, transfer the pseudo-fingerprint pattern onto the surface of the optical disk to be evaluated by pressing the transferring stamp, on which a portion of the artificial fingerprint liquid material has removed off, against the surface of the optical disk, under a predetermined load of 1 N to 35 N for a predetermined period of time. The load and the time over which the load is applied are also properly determined.

Level 3:

1. Transfer the artificial fingerprint liquid material applied to the surface of the master plate onto the pseudo-fingerprint transferring stamp by pressing the transferring stamp against the surface of the master plate on which the artificial fingerprint liquid is applied, under a predetermined load of 1 N to 35 N for a predetermined period of time. The load and the time over which the load is applied are properly determined.

2. Subsequently, transfer a portion of the transferred artificial fingerprint liquid material onto the transferring stamp, onto the surface of a polycarbonate substrate (e.g., polcarbonate substrate that has an identical shape to the optical disk to be evaluated) by pressing the transferring stamp with the transferred artificial fingerprint liquid material against the surface of the polycarbonate substrate, under a predetermined load of 1 N to 35 N for a predetermined period of time. The load and the time over which the load is applied are also properly determined.

3. Subsequently, further transfer an additional portion of the artificial fingerprint liquid material on the transferring stamp onto a different area of the surface of the polycarbonate substrate by pressing again the transferring stamp, on which a portion of the artificial fingerprint liquid material has removed off, against the different area of the surface of the polycarbonate substrate, under a predetermined load of 1 N to 35 N for a predetermined period of time. The load and the time over which the load is applied are also properly determined.

4. Subsequently, transfer the pseudo-fingerprint pattern onto the surface of the optical disk to be evaluated by pressing the transferring stamp, on which a portion of the artificial fingerprint liquid material has removed off twice, against the surface of the optical disk, under a predetermined load of 1 N to 35 N for a predetermined period of time. The load and the time over which the load is applied are also properly determined.

Level 4:

1. Transfer the artificial fingerprint liquid material applied to the surface of the master plate onto the pseudo-fingerprint transferring stamp by pressing the transferring stamp against the surface of the master plate on which the artificial fingerprint liquid is applied, under a predetermined load of 1 N to 35 N for a predetermined period of time. The load and the time over which the load is applied are properly determined.

2. Subsequently, transfer a portion of the transferred artificial fingerprint liquid material onto the transferring stamp, onto the surface of a polycarbonate substrate (e.g., polycarbonate substrate that has an identical shape to the optical disk to be evaluated) by pressing the transferring stamp with the transferred artificial fingerprint liquid material against the surface of the polycarbonate substrate, under a predetermined load of 1 N to 35 N for a predetermined period of time. The load and the time over which the load is applied are also properly determined.

3. Subsequently, further transfer an additional portion of the artificial fingerprint liquid material on the transferring stamp onto a different area of the surface of the polycarbonate substrate by pressing again the transferring stamp, on which a portion of the artificial fingerprint liquid material has removed off, against the different area of the surface of the polycarbonate substrate, under a predetermined load of 1 N to 35 N for a predetermined period of time. The load and the time over which the load is applied are also properly determined.

4. Repeat the procedure 3 above.

5. Subsequently, transfer the pseudo-fingerprint pattern onto the surface of the optical disk to be evaluated by pressing the transferring stamp, on which a portion of the artificial fingerprint liquid material has removed off three times, against the surface of the optical disk, under a predetermined load of 1 N to 35 N for a predetermined period of time. The load and the time over which the load is applied are also properly determined.

As the level of the transfer process increases from the above-described level 1 to level 4, the amount of the artificial fingerprint liquid transferred to the surface of the optical disk to be evaluated decreases correspondingly. When it is desired to determine the characteristic quality of the optical disk by a decreased amount of the fingerprint liquid adhered to the disk surface, the level of the transfer process may be raised.

In the present invention, the artificial fingerprint liquid is preferably a liquid obtained by: adding a diluent selected from isopropyl alcohol, methyl ethyl ketone and methoxypropanol to a mixture of Kanto loam having an average particle size of 0.5 μm or more and 10 μm or less (JIS Z8901 testing powder) as the fine-particle-form substance and triolein in a weight ratio of Kanto loam to triolein of 0.2 to 1.0.

In the present invention, the transferring stamp is preferably a product obtained by rubbing the circular surface of rubber plug having a diameter of 8 to 20 mm with an AA240 abrasive material prescribed in JIS R6251 or JIS R6252, or with an equivalent abrasive material to make the surface rough.

The use of the above-described method makes it possible that the artificial fingerprint liquid is adhered onto the recording/reproducing beam incident side surface of the optical disk with a good reproducibility.

As an observing index of the state of the artificial fingerprint liquid droplets adhered under predetermined conditions onto the recording/reproducing beam incident side surface of the optical disk, in the present invention, an area ratio of the disk surface occupied with the artificial fingerprint liquid droplets adhered per unit area of the disk surface is measured. However, indices other than the area ratio, such as the diameter, the perimeter, the relationship between the perimeter and the area (i.e., degree of roundness), the absolute maximum length, the aspect ratio, the number, the distance between centers of gravity, and the area distribution of area ratio of the artificial fingerprint liquid droplets adhered onto the disk surface may also used. Furthermore, the maximum value, the minimum value, the mean value, the total value, the proportion, and the standard deviation of droplets may be suitably used for each of these indices.

(Evaluation by Measuring the Area Ratio of the Disk Surface Occupied with the Artificial Fingerprint Liquid Droplets Adhered Per Unit Area of the Disk Surface)

In the present invention, as described above, the artificial fingerprint liquid is adhered, under predetermined conditions, onto the recording/reproducing beam incident side surface of an optical disk. And then, the area ratio of the disk surface occupied with the artificial fingerprint liquid droplets adhered per unit area of the disk surface is measured. The optical disk is judged as an acceptable disk when the measured area ratio is 6% or less.

The state of the droplets of the artificial fingerprint liquid adhered to the surface of the optical disk is observed with an optical microscope, and its images are processed on a computer to determine the area ratio of the disk surface occupied with the artificial fingerprint liquid droplets using image-processing technology. Using image-processing technology, the area ratio can be obtained simply by dividing the artificial fingerprint liquid droplets-adhered portion and droplets-free portion into 2-value, measuring respective areas.

Considering the spot size of laser beam, the artificial fingerprint liquid droplets less than 5 μm in diameter adhered to the disk surface are considered to hardly affect the focusing and tracking characteristics of laser beam. Therefore, in measurement of focusing and tracking characteristics, the artificial fingerprint liquid droplets less than 5 μm in diameter may be ignored for the convenience (namely, considered as the artificial fingerprint liquid droplets-free portion) to effect the above measurement. However, in measurement of recording and/or reproducing signals such as error rates, even such small artificial fingerprint liquid droplets can affect the measurement. Thus, the artificial fingerprint liquid droplets less than 5 μm in diameter should be taken into account in measuring these signals. As used herein, "the diameter of the artificial fingerprint liquid droplet" is determined by measuring the area of the artificial fingerprint liquid droplet adhered to the disk surface, assuming that each artificial fingerprint liquid droplet is a perfect circle, and calculating the diameter of the perfect circle from the area of individual droplet.

In case of using an artificial fingerprint liquid described in Examples, it has been demonstrated that when the area ratio of the disk surface occupied with the artificial fingerprint liquid droplets exceeds 6%, the error rate becomes unfavorable. Thus, for evaluation of an optical information medium, the optical information medium in which this area ratio is 6% or less may be judged as an acceptable medium. Further, for safety, a specific area ratio value smaller than 6% may be suitably determined, the optical information medium having the area ratio not more than the specific area ratio value may be judged as an acceptable medium. For example, in case the medium having the area ratio not more than 1% is judged as an acceptable medium, only the medium having the very favorable error rate can be judged as an acceptable medium.

(Evaluation by Measuring the Recording and/or Reproducing Characteristic of Optical Disk with the Artificial Fingerprint Liquid Droplets Adhered to the Disk Surface)

And, in the present invention, as described above, the artificial fingerprint liquid is adhered, under predetermined conditions, onto the recording/reproducing beam incident side surface of an optical disk. And then, the recording and/or reproducing characteristic of the optical disk is measured with the artificial fingerprint liquid droplets adhered to the surface. The optical disk is judged as an acceptable disk when the measured recording and/or reproducing characteristic is equal to, or better than, a predetermined value. The predetermined value of the recording/reproducing characteristic may be suitably determined based on the performance level required of the optical disk to be evaluated.

The recording/reproducing characteristic to be measured is not particularly limited, and examples thereof include reflectance, degree of modulation, and RF signals flatness during the reproducing process of the medium; jitter, output level, carrier-to-noise ratio (CN ratio), and error rate of any of recorded signals, erasable signals, and non-erasable signals; and peak-to-peak (p-p) value of a focus/sensitivity curve obtained for the line speed during the recording or reproducing process, the amount of residual error of focus error signals, and the ratio of the p-p value to the residual error. One or more of these characteristics may be measured as the standard for evaluation. The focus/sensitivity curve assumes what is commonly known as a sigmoid curve and is described in page 81 of "*Optical disk Technology*" published on Feb. 10th, 1988, by Radio Technology Co.,Ltd. From the focus/sensitivity curve, the p-p value of the focus error signals output, namely the difference between the peak value of positive output and the peak value of negative output is obtained to be represented as "F". On the other hand, the output p-p value of the residual error of focus error signals is obtained to be represented as "R". If the value R/F is small, specifically 10% or less, then the jitter generated during the reproducing process becomes sufficiently small and writing errors are significantly reduced.

(Evaluation by Measuring the Error Rate of Optical Disk with the Artificial Fingerprint Liquid Droplets Adhered to the Disk Surface)

In the present invention, as described above, the error rate can be measured as the recording and/or reproducing characteristic of an optical disk. Namely, the evaluation dispersion liquid, which contains a fine-particle-form substance and a dispersion medium capable of dispersing the fine-particle-form substance, is adhered, under predetermined conditions, onto the recording/reproducing beam incident side surface of an optical information medium. And then, the error rate as a recording and/or reproducing characteristic of the medium is measured, with the evaluation dispersion liquid droplets adhered to the medium surface. The optical information medium is judged as an acceptable medium when the measured error rate is equal to, or smaller than, a predetermined value. The term "error rate" refers to known error rates such as bit-by-bit error rate and symbol error rate. The predetermined value for the error rate maybe suitably determined based on the performance level required of the optical disk to be evaluated. In general, bit-by-bit error rate or symbol error rate of $10^{-4}$ or smaller are small enough for practical use.

Further, in evaluation of optical disk surface, the artificial fingerprint liquid may be transferred to the surface of a data-recorded optical disk and the data is subsequently read out, or alternatively, the artificial fingerprint liquid may be transferred to the surface of an unrecorded optical disk and the data is subsequently recorded and read out.

The evaluation method of the present invention is applied to evaluate the surface quality of the optical disk such as a reproduction-only optical disk, optical recording disk, magneto-optical recording disk, and the like, and is preferably applied to the optical information medium intended for use in a system wherein the smallest diameter of the recording/reproducing beam on the surface which is on the incident side of the recording/reproducing beam is 500 µm or less. As for such an optical information medium, if fingerprints or other stains are adhered on the recording/reproducing beam incident side surface of the medium during use of the medium, deterioration problem of recording and/or reproducing characteristics, such as error rates is particularly liable to occur.

Needless to say, the evaluation method of the present invention is also applicable to the optical information medium intended for use in a system wherein the smallest diameter of the recording/reproducing beam on the surface which is on the incident side of the recording/reproducing beam is greater than 500 µm.

A structural example of an optical information medium to which the present invention is applied is shown in FIG. 1. This optical information medium is a recording medium, and comprises a recording layer (4) that functions as an information recording layer on a supporting substrate (20) of comparatively high rigidity, a light-transmitting layer (7) on the recording layer (4), and a light transmitting hard coat layer (8) on the light-transmitting layer (7). The hard coat layer (8) acts as the surface upon which the recording/reproducing beam is incident, and the laser beam for recording or reproducing is incident through the hard coat layer (8) and the light-transmitting layer (7), and onto the recording layer (4). The thickness of the light-transmitting layer (7), including the hard coat layer (8), is preferably within a range from 30 to 300 µm, and even more preferably from 70 to 150 82 m. A thin anti-staining surface layer that shows a high water repellency and a high oil repellency may be further formed on the hard coat layer (8).

Influence, based on adhesion of a fingerprint, on recording/reproducing property depends on the diameter of a laser beam (the smallest diameter in the case that the beam section is elliptic) on the medium surface which is on the incident side of the laser beam. When this diameter is small, large influences as follows are produced: continuous errors, which cannot be corrected, are made. The present inventors' research has demonstrated that in the case that the diameter of the laser beam incident side surface of the medium is 500 µm or less, in particular, 300 µm or less, bad influence on the recording/reproducing property becomes remarkable when a fingerprint adheres to the medium which is being handled. The diameter of the laser beam, on the laser beam incident side surface of the medium, is represented as follows:

$$2t \cdot \tan\{\sin^{-1}(NA/n)\}$$

wherein the thickness of the light-transmitting layer (7) in FIG. 1 is represented by t, the refractive index of the light-transmitting layer (7) is represented by n, and the numerical aperture of the objective lens of the recording/reproducing optical system is represented by NA. It should be noted that in this term, the hard coat layer is neglected since the difference in refractive index between the hard coat layer (8) and the light-transmitting layer (7) is small enough and the hard coat layer (8) is significantly thinner than the light-transmitting layer (7).

The present invention can be applied regardless of the kind of the recording layer. That is, the present invention can be applied to a recording medium whether the medium is, for example, a phase-change type recording medium, a bit-forming type recording medium or a magneto-optical recording medium. Usually, a dielectric layer or a reflective layer for protecting the recording layer or attaining an optical effect is laid on at least one side of the recording layer. However, the above laid layer is not shown in FIG. 1. The present invention can be applied to a reproduction-only type, as well as a recordable type as illustrated. In this case, a pit row integrated with the supporting substrate (20) is formed, and a reflective layer (metal layer or dielectric multilayered film) covering the pit row constitutes an information recording layer.

Figure 2:
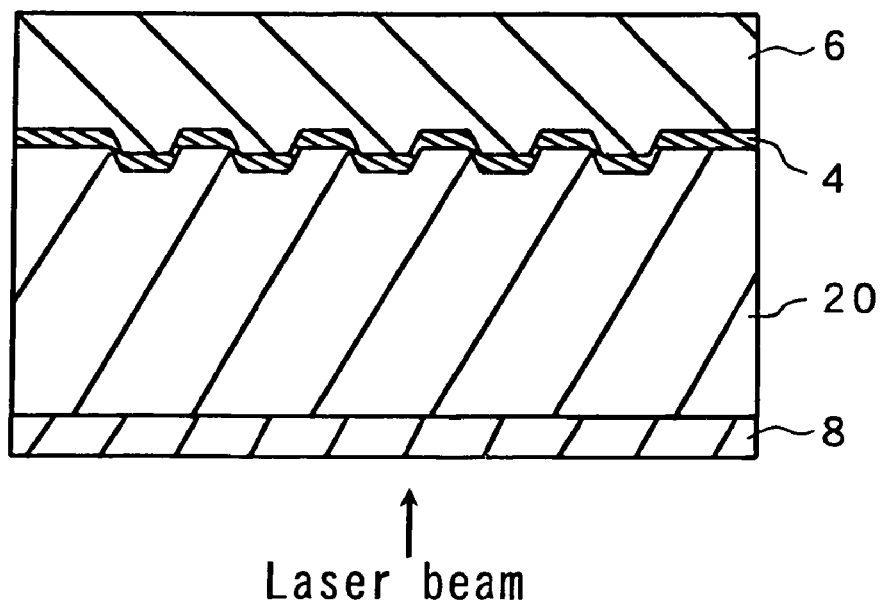
FIG. 2 is a schematic cross-sectional view illustrating another structural example of the optical information medium.

The present invention can also be applied to an optical information medium of a structural example shown in FIG. 2. The medium illustrated in FIG. 2 comprises an information recording layer (4) on one surface of a light transmitting supporting substrate (20), and a protective layer (6) on the information recording layer (4), whereas a light-transmitting hard coat layer (8) is formed on the other surface of the supporting substrate (20). The hard coat layer (8) acts as the surface upon which the recording/reproducing beam is incident, and the laser beam for recording or reproducing is incident through the hard coat layer (8) and the supporting substrate (20), and onto the recording layer (4).

The two media each having the structure illustrated in FIG. 1 or FIG. 2 are adhered to each other so as to cause the hard coat layers (8) to face outwards, so that a two-sided recording type medium can be produced.

EXAMPLES

The present invention will be more specifically described by way of the following examples. However, the present invention is not limited to these examples.

[Production of Disk Sample A]

Figure 3:
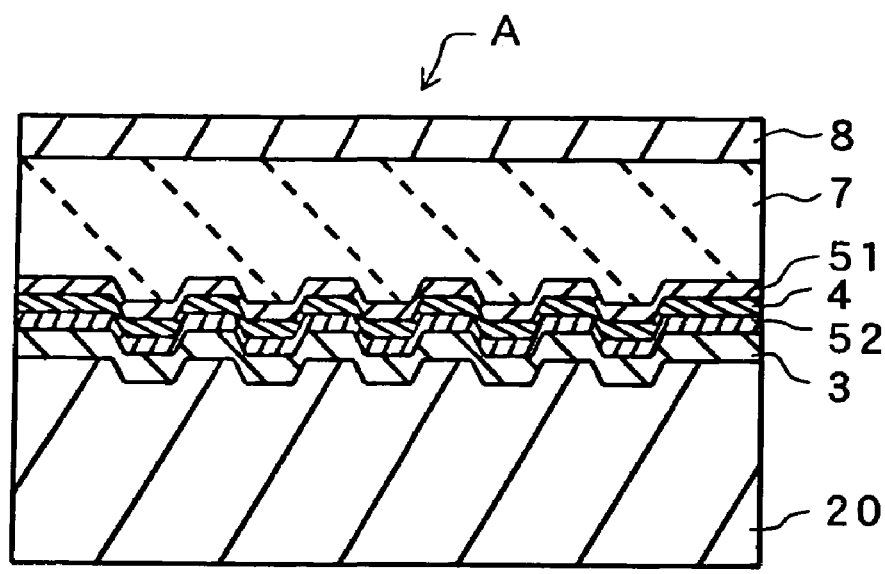
FIG. 3 is a schematic cross-sectional view of an optical recording disk sample used in Example.

An optical recording disk sample A with the layer structure shown in FIG. 3 was produced. In FIG. 3, the optical disk A has a supporting substrate (20) having information pits, pregrooves, and other fine scale concavities-convexities formed on one surface thereof. On this surface, the optical disk has a reflective layer (3), a second dielectric layer (52), a recording layer (4), and a first dielectric layer (51) formed in this order., and further has a light-transmitting layer (7) on the first dielectric layer (51), and a hard coat layer (8) on the light transmitting layer (7). When using the optical disk (1), a laser beam for recording or reproducing is incident through the hard coat layer (8) and the light transmitting layer (7).

Using a disk shaped supporting substrate (20) (formed from polycarbonate, diameter 120 mm, thickness 1.1 mm) in which information recording grooves had been formed, sputtering was used to form a reflective layer (3) of thickness 100 nm comprising $Al_{98}Pd_1Cu_1$ (atomic ratio) on the groove-side surface of the substrate. The depth of the grooves, which is represented by light-path length at a wavelength $\lambda=405$ nm, was set into $\lambda/6$. The recording track pitch in the groove-recording scheme was set into 0.3 µm.

Subsequently, sputtering with an $Al_2O_3$ target was used to form a second dielectric layer (52) of thickness 20 nm on the surface of the reflective layer (3). Sputtering using an alloy target comprising a phase-changing material was then used to form a recording layer (4) of thickness 12 nm on the surface of the second dielectric layer (52). The composition (atomic ratio) of the recording layer (4) was $Sb_{74}Te_{18}$ $(Ge_7In_1)$. Sputtering with a ZnS (80 mol %)-$SiO_2$ (20 mol %) target was then used to form a first dielectric layer (51) of thickness 130 nm on the surface of the recording layer (4).

Subsequently, a radical polymerizable, ultraviolet ray-curable material with the composition shown below was applied onto the surface of the first dielectric layer (51) by spin coating, and was then irradiated with ultraviolet rays, thus forming a light transmitting layer (7) with a cured thickness of 98 µm.

| (Light transmitting layer: composition of the ultraviolet ray-curable material) | |
|---|---|
| Urethane acrylate oligomer (Diabeam UK6035, manufactured by Mitsubishi Rayon Co., Ltd.) | 50 parts by weight |
| Isocyanuric acid EO modified triacrylate (Aronix M315, manufactured by Toagosei Co., Ltd.) | 10 parts by weight |
| Isocyanuric acid EO modified diacrylate (Aronix M215, manufactured by Toagosei Co., Ltd.) | 5 parts by weight |
| Tetrahydrofurfuryl acrylate | 25 parts by weight |
| Photopolymerization initiator (1-hydroxycyclohexyl phenyl ketone) | 3 parts by weight |

Subsequently, an ultraviolet ray/electron ray-curable hard coat agent with the composition shown below was applied onto the light transmitting layer (7) by spin coating to form a coating layer, and the applied coating layer was then heated at 60° C. for 3 minutes in an atmosphere to remove the diluent in the coating layer. And then, the coating layer was irradiated with ultraviolet rays to form the hard coat layer (8) having a cured thickness of 2 µm. In this manner, the disk sample A was prepared.

| (Composition of the hard coat agent) | |
|---|---|
| Reactive group modified colloidal silica (dispersion medium: propyleneglycolmonomethylether acetate, nonvolatile content: 40% by weight) | 100 parts by weight |
| Dipentaerythritol hexaacrylate | 48 parts by weight |
| Tetrahydrofurfuryl acrylate | 12 parts by weight |
| Propyleneglycol monomethylether acetate (unreactive diluent) | 40 parts by weight |
| IRGACURE 184 (polymerization initiator) | 5 parts by weight |
| Bifunctional silicone methacrylate (X-22-164A, manufactured by Shin-Etsu Chemical Co., Ltd.) | 0.25 part by weight |

[Production of Disk Sample B]

Figure 4:
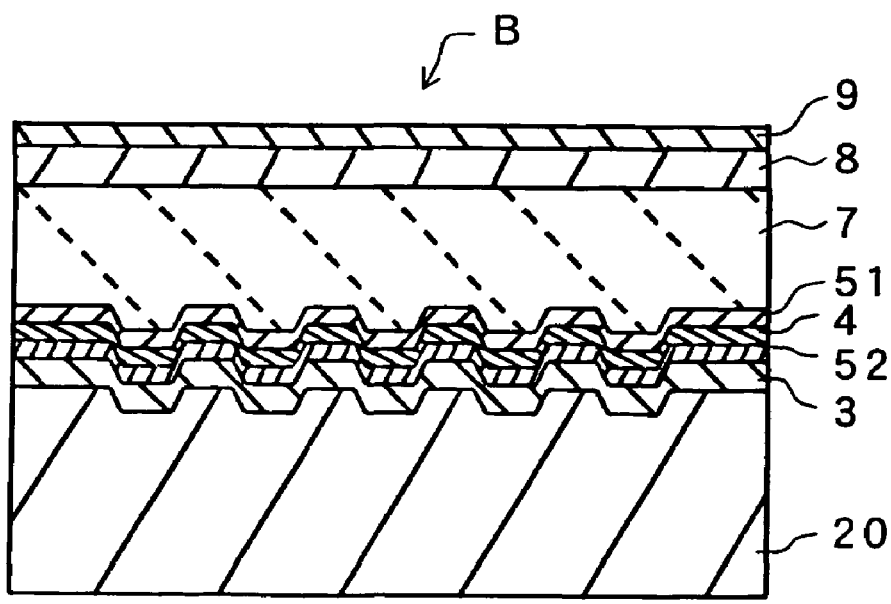
FIG. 4 is a schematic cross-sectional view of an optical recording disk sample used in Example.

An optical recording disk sample B with the layer structure shown in FIG. 4 was produced. The optical disk B of FIG. 4 further includes an anti-staining surface layer (9) on the hard coat layer (8) of the optical disk A of FIG. 3. When using the optical disk B, a laser beam for recording or reproducing is incident through the anti-staining surface layer (9), the hard coat layer (8) and the light transmitting layer (7).

The same procedures were followed as in the production of the optical disk A up to the formation of the light transmitting layer (7).

An ultraviolet ray/electron ray-curable hard coat agent with the composition shown below was applied onto the light transmitting layer (7) by spin coating to form a coating layer, and the applied coating layer was then heated at 60° C. for 3 minutes in an atmosphere to remove the diluent in the coating layer. And then, the coating layer was irradiated with ultraviolet rays to form the hard coat layer (8) having a cured thickness of 2 µm.

| Composition of the hard coat agent | |
|---|---|
| Reactive group modified colloidal silica (dispersion medium: propyleneglycolmonomethylether acetate, nonvolatile content: 40% by weight) | 100 parts by weight |

-continued

| Composition of the hard coat agent | |
|---|---|
| Dipentaerythritol hexaacrylate | 48 parts by weight |
| Tetrahydrofurfuryl acrylate | 12 parts by weight |
| Propyleneglycol monomethylether acetate (unreactive diluent) | 40 parts by weight |
| IRGACURE 184 (polymerization initiator) | 5 parts by weight |

Further, an ultraviolet ray/electron ray-curable fluorine-containing anti-staining agent with the composition shown below was applied onto the hard coat layer (8) by spin coating to form a coating layer, and the applied coating layer was then heated at 60° C. for 3 minutes in an atmosphere to remove the diluent in the coating layer. And then, the coating layer was irradiated with electron electron rays to form the anti-staining surface layer (9) having a cured thickness of approximately 30 nm. In this manner, the disk sample B was prepared.

| (Composition of the anti-staining agent) | |
|---|---|
| Perfluoropolyether diacrylate (An acrylate-modified product of Fomblin ZDOL, manufactured by Ausimont Co., Ltd., Molecular Weight: about 2,000) | 1 part by weight |
| 3-perfluorooctyl-2-hydroxypropylacrylate (R-1833, manufactured by Daikin Fine Chemical Laboratory Co., Ltd.) | 3 parts by weight |
| Fluorine-containing solvent (FLUORINERT FC-77, manufactured by Sumitomo 3M Co., Ltd.) | 1600 parts by weight |

[Preparation of Artificial Fingerprint Liquid and Adhesion to the Disk Samples]

(Preparation of Artificial Fingerprint Liquid)

0.4 parts by weight of Kanto loam of class 11 testing powder 1 (median diameter: 1.6 to 2.3 μm) prescribed in JIS Z8901 as the fine-particle-form substance, 1 part by weight of triolein as the dispersion medium, and 10 parts by weight of methoxypropanol as the diluent were mixed and stirred to form an artificial fingerprint liquid.

(Formation of Master Plate for Transferring Pseudo-fingerprint Patterns)

A master plate for transferring pseudo-fingerprint patterns was produced as follows. While the artificial fingerprint liquid was sufficiently stirred with a magnetic stirrer, an approximately 1 mL portion of the liquid was collected. The collected liquid was applied onto a polycarbonate substrate (diameter: 120 mm, thickness: 1.2 mm) by spin coating. Spin coating was carried out at 500 rpm for 2 seconds, followed by 250 rpm for 2 seconds. This substrate was heated at 60° C. for 3 minutes to completely remove methoxypropanol, which was the diluent which had become unnecessary. In this way, master plate for transferring pseudo-fingerprint patterns was obtained.

(Transfer of Pseudo-fingerprint Patterns to the Surface of Disk Samples)

The artificial fingerprint liquid material was transferred onto the surface of the hard coat layer (8) or the anti-staining surface layer (9) of the respective disk samples at the following adhesion levels 1 through 4.

Adhesion Level 1:

A No. 1. silicone rubber plug was uniformly rubbed with a #240 abrasive paper (having the equivalent performance to AA240 abrasive paper described in the above JIS) on its smaller end surface (diameter: 12 mm) and was used as the pseudo-fingerprint transferring stamp. The rubbed end surface of the pseudo-fingerprint transferring stamp was pressed against the master plate with a load of 4.9 N for 10 seconds to transfer the artificial fingerprint liquid material to the end surface of the transferring stamp. Subsequently, the end surface of the transferring stamp, onto which the artificial fingerprint liquid material adhered, was pressed against an area of the surface of the hard coat layer (8) or the anti-staining surface layer (9) of the respective disk samples, the area being located about 40 mm apart in the radius direction from the center the disk, with a load of 4.9 N for 10 seconds to transfer the artificial fingerprint liquid material.

Adhesion Level 2:

As in the Adhesion Level 1, the rubbed end surface of another pseudo-fingerprint transferring stamp was pressed against the master plate with a load of 4.9 N for 10 seconds to transfer the artificial fingerprint material to the end surface of the transferring stamp. Subsequently, the end surface of the transferring stamp, onto which the artificial fingerprint liquid material adhered, was pressed against the smooth surface of a polycarbonate substrate with a load of 4.9 N for 10 seconds to reduce the adhesion amount of artificial fingerprint liquid material on the end surface of the transferring stamp. The end surface of the transferring stamp, on which the adhesion amount was reduced, was pressed against an area of the surface of the hard coat layer (8) or the anti-staining surface layer (9) of the respective disk samples, the area being located about 40 mm apart in the radius direction from the center the disk, with a load of 4.9 N for 10 seconds to transfer the artificial fingerprint liquid material.

Adhesion Level 3:

The step taken in Adhesion Level 2 of reducing the adhesion amount was repeated twice by pressing the end surface of the transferring stamp, onto which the artificial fingerprint liquid material adhered, against a polycarbonate substrate twice successively with a load of 4.9 N for 10 seconds but on separate locations on the polycarbonate substrate. This further reduced the adhesion amount of artificial fingerprint liquid material on the end surface of the transferring stamp. The rest of the process was carried out in the same manner as in Adhesion Level 2 to transfer the artificial fingerprint liquid material onto the surface of the hard coat layer (8) or the anti-staining surface layer (9) of the respective disk samples.

Adhesion Level 4:

The step taken in Adhesion Level 2 of reducing the adhesion amount was repeated three times by pressing the end surface of the transferring stamp, onto which the artificial fingerprint liquid material adhered, against a polycarbonate substrate three times successively with a load of 4.9 N for 10 seconds but on separate locations on the polycarbonate substrate. This further reduced the adhesion amount of artificial fingerprint liquid material on the end surface of the transferring stamp. The rest of the process was carried out in the same manner as in Adhesion Level 2 to transfer the artificial fingerprint liquid material onto the surface of the hard coat layer (8) or the anti-staining surface layer (9) of the respective disk samples.

[Evaluation of Disk Samples]

(Measurement of the Area Ratio of the Surface Occupied with the Artificial Fingerprint Liquid Droplets Adhered Per Unit Area of the Surface)

The state of the droplets of the artificial fingerprint liquid adhered to the surface of each disk sample was observed with an optical microscope (VK-8510, manufactured by Keyence Co., Ltd.). This image was printed on a printer (VH-P40, manufactured by Keyence Co., Ltd.). And the image was read and was processed on a computer to determine the area ratio of the surface area occupied with the artificial fingerprint liquid droplets to the whole surface area, by using an image-processing/analysis software Win ROOF, ver. 3.61 (Demonstration version, manufactured by Mitani Corporation). The analysis included the artificial fingerprint liquid droplets less than 5 µm in diameter.

(Measurement of Error Rate)

Information was recorded on each disk sample, and then the bit-by-bit error rate (bER) was measured on an evaluation apparatus for optical recording media (DDU-1000, manufactured by Pulstec Industrial Co., Ltd., wavelength $\lambda=405$ nm, NA=0.85) to give an initial error rate. The disk sample A had an initial error rate of 0, while the disk sample B had an initial error rate of $1\times10^{-1}$. Next, the artificial fingerprint liquid droplets were adhered onto the surface of each disk sample at each operation of Adhesion Level 1 through Adhesion Level 4, and the error rate (bER) was measured with the artificial fingerprint liquid droplets adhered to the disk surface. 10 disk samples were used for each Adhesion Level and the average value was determined.

The results of the above measurements are shown in Table 1 below.

TABLE 1

| | Disk A | | | | Disk B | | | |
|---|---|---|---|---|---|---|---|---|
| Level | Area ratio | Judgement | bER | Judgement | Area ratio | Judgement | bER | Judgement |
| 1 | 10.8% | Defective | $3 \times 10^{-3}$ | Defective | 4.9% | Acceptable | $2 \times 10^{-6}$ | Acceptable |
| 2 | 9.6% | Defective | $2 \times 10^{-4}$ | Defective | 1.0% | Acceptable | $2 \times 10^{-7}$ | Acceptable |
| 3 | 6.0% | Acceptable | $6 \times 10^{-5}$ | Acceptable | 0.9% | Acceptable | $1 \times 10^{-6}$ | Acceptable |
| 4 | 5.2% | Acceptable | $7 \times 10^{-6}$ | Acceptable | 0.2% | Acceptable | $2 \times 10^{-7}$ | Acceptable |

As can be seen from Table 1, when the transferring operation was carried out using the same condition, less amounts of the artificial fingerprint liquid droplets adhered to the surface of the respective disk samples B than the amounts of the artificial fingerprint liquid droplets adhered to the corresponding disk samples A. This indicates that the disk samples B have a better anti-staining property than the disk samples A.

When the transferring operation was carried out at Adhesion Levels 1 and 2, the area ratios of the surface area of the respective disk samples A occupied with the adhered artificial fingerprint liquid droplets were 10.8% and 9.6%, each larger than 6.0%. Thus, each disk sample A was judged as defective. At the same Adhesion Levels, the area ratios of the surface area of the respective disk samples B occupied with the adhered artificial fingerprint liquid droplets were 4.9% and 1.0%, each not more than 6.0%. Thus, each disk sample B was judged as acceptable. When the transferring operation was carried out at Adhesion Levels 3 and 4, the area ratios of the surface area of the respective disk samples A occupied with the adhered artificial fingerprint liquid droplets were 6.0% and 5.2%, each not more than 6.0%. Thus, each disk sample A was judged as acceptable. At the same Adhesion Levels, the area ratios of the surface area of the respective disk samples B occupied with the adhered artificial fingerprint liquid droplets were 0.9% and 0.2%, each not more than 6.0%. Thus, each disk sample B was also judged as acceptable.

These results show that the conditions for transferring operation may be suitably determined based on the level of the surface performance required of an optical disk to be evaluated. That is, in case where the optical disk is considered unacceptable even if it has as high a surface performance as the disk sample A and is required to have a higher surface performance comparable to that of the disk sample B, by carrying out the transferring operation at Adhesion Levels 1 or 2, the disk samples A and B are respectively judged as defective and acceptable on the basis of the difference between surface performances of both disk samples A and B. And, when an optical disk with as high a surface performance as that of the disk sample A is considered as acceptable, the transferring operation may be carried out at Adhesion Levels 3 or 4.

The area ratio value of the surface occupied with the artificial fingerprint liquid droplets was correlated with the error rate value measured with the artificial fingerprint liquid droplets adhered to the disk surface. This clearly shows that the surface performance of an optical disk can be evaluated by determining the error rate with the artificial fingerprint liquid droplets adhered to the disk surface, instead of determining the area ratio of the surface occupied with the artificial fingerprint liquid droplets. When the error rate is used in the evaluation, a threshold value of error rate is suitably predetermined based on the performance level required of an optical disk to be evaluated, and the optical disk is judged as acceptable if the error rate is less than or equal to the threshold value. In the present examples, one example is described in which judgement of acceptable or defective was carried out based on the threshold error rate value of $1\times10^{-4}$. In general, error rates of $1\times10^{-4}$ or smaller are sufficient for practical use.

As set forth, it has been demonstrated-that the area ratio value of the artificial fingerprint liquid droplets, or the error rate value as the recording/reproducing characteristic can be used as a standard for judging the quality of the optical disk. The components and composition of the artificial fingerprint liquid (i.e., evaluation dispersion liquid), conditions for adhering the artificial fingerprint liquid, and the predetermined values of recording/reproducing characteristics are appropriately determined based on the surface performance level required of an optical disk to be evaluated.

The invention claimed is:

1. A method for evaluating an optical information medium, comprising the steps of:
    adhering, under predetermined conditions, an evaluation dispersion liquid containing a fine-particle-form substance and a dispersion medium capable of dispersing the fine-particle-form substance onto the surface of the optical information medium which is on the incident side of a recording or reproducing beam;

measuring a recording or reproducing characteristic of the medium with the evaluation dispersion liquid droplets adhered to the medium surface; and judging the optical information medium as an acceptable medium when the measured recording or reproducing characteristic is equal to, or better than, a predetermined value.

2. A method for evaluating an optical information medium, comprising the steps of:

adhering, under predetermined conditions, an evaluation dispersion liquid containing a fine-particle-form substance and a dispersion medium capable of dispersing the fine-particle-form substance onto the surface of the optical information medium which is on the incident side of a recording or reproducing beam;

measuring the error rate as a recording or reproducing characteristic of the medium, with the evaluation dispersion liquid droplets adhered to the medium surface; and judging the optical information medium as an acceptable medium when the measured error rate is equal to, or smaller than, a predetermined value.

* * * * *